(12) United States Patent
Tanaka et al.

(10) Patent No.: US 7,226,462 B2
(45) Date of Patent: *Jun. 5, 2007

(54) SPECIALLY SHAPED BALLOON DEVICE FOR USE IN SURGERY AND METHOD OF USE

(75) Inventors: Shigeru Tanaka, Menlo Park, CA (US); Gary Ashley Stafford, Hayward, CA (US)

(73) Assignee: General Surgical Innovations, Inc., North Haven, CT (US)

( * ) Notice: Subject to any disclaimer, the term of this patent is extended or adjusted under 35 U.S.C. 154(b) by 6 days.

This patent is subject to a terminal disclaimer.

(21) Appl. No.: 10/865,515

(22) Filed: Jun. 10, 2004

(65) Prior Publication Data

US 2004/0243167 A1 Dec. 2, 2004

Related U.S. Application Data

(63) Continuation of application No. 09/322,201, filed on May 28, 1999, now Pat. No. 6,860,892.

(51) Int. Cl.
*A61B 17/00* (2006.01)
*A61B 1/32* (2006.01)
*A61M 29/02* (2006.01)

(52) U.S. Cl. .................. 606/190; 600/207; 604/103.07

(58) Field of Classification Search ..... 604/96.01–112; 606/190–200, 213; 600/201, 204, 207
See application file for complete search history.

(56) References Cited

U.S. PATENT DOCUMENTS

| | | | |
|---|---|---|---|
| 1,863,057 A | 6/1932 | Innes | |
| 1,909,967 A | 5/1933 | Jones | |
| 2,854,983 A | 10/1958 | Baskin | |
| 2,936,760 A | 5/1960 | Gants | |
| 3,039,468 A | 6/1962 | Price | |
| 3,253,594 A | 5/1966 | Matthews et al. | |
| 3,397,699 A | 8/1968 | Kohl | |
| 3,416,160 A | 12/1968 | Arion | |
| 3,417,745 A | 12/1968 | Sheldon | |
| 3,459,175 A | 8/1969 | Miller | |
| 3,495,586 A | 2/1970 | Regenbogen | |
| 3,557,794 A | 1/1971 | Van Patten | |
| 3,774,596 A | 11/1973 | Cook | |
| 3,800,788 A | 4/1974 | White | |

(Continued)

FOREIGN PATENT DOCUMENTS

FR 2580504 10/1986

(Continued)

OTHER PUBLICATIONS

R. Wittmoser, *Retroperitoneoscopy*: A Preliminary Report, pp. 760-761.

(Continued)

*Primary Examiner*—Glenn K. Dawson

(57) ABSTRACT

A balloon device useful for dissecting tissue or retracting tissue for the purpose of providing access for laparoscopic surgery, the device including a balloon which inflates to a shape specially suitable for the surgical procedure and the anatomical region of deployment. The present device, when configured with a tapered dissection balloon, is particularly useful for subfascial endoscopic perforator surgical procedures.

14 Claims, 7 Drawing Sheets

U.S. PATENT DOCUMENTS

| | | | |
|---|---|---|---|
| 3,882,852 A * | 5/1975 | Sinnreich | 600/104 |
| 3,915,171 A | 10/1975 | Shermeta | |
| 4,077,412 A | 3/1978 | Moossun | |
| 4,083,369 A | 4/1978 | Sinnreich | |
| 4,177,814 A | 12/1979 | Knepshield et al. | |
| 4,198,981 A | 4/1980 | Sinnreich | |
| 4,295,464 A | 10/1981 | Shihata | |
| 4,312,353 A | 1/1982 | Shahbabian | |
| 4,501,266 A | 2/1985 | McDaniel | |
| 4,555,242 A | 11/1985 | Saudagar | |
| 4,572,186 A | 2/1986 | Gould et al. | |
| 4,585,000 A | 4/1986 | Hershenson | |
| 4,589,868 A | 5/1986 | Dretler | |
| 4,608,965 A | 9/1986 | Anspach, Jr. et al. | |
| 4,610,662 A | 9/1986 | Weikl et al. | |
| 4,630,609 A | 12/1986 | Chin | |
| 4,651,717 A | 3/1987 | Jakubczak | |
| 4,681,093 A | 7/1987 | Ono et al. | |
| 4,706,670 A | 11/1987 | Andersen et al. | |
| 4,714,074 A | 12/1987 | Rey et al. | |
| 4,779,611 A | 10/1988 | Grooters et al. | |
| 4,796,629 A | 1/1989 | Grayzel | |
| 4,798,205 A | 1/1989 | Bonomo et al. | |
| 4,800,901 A | 1/1989 | Rosenberg | |
| 4,802,479 A | 2/1989 | Haber et al. | |
| 4,861,334 A | 8/1989 | Nawaz | |
| 4,875,468 A | 10/1989 | Krauter et al. | |
| 4,899,729 A | 2/1990 | Gill et al. | |
| 4,921,478 A | 5/1990 | Solano et al. | |
| 4,927,412 A | 5/1990 | Menasche | |
| 4,932,956 A | 6/1990 | Reddy et al. | |
| 4,932,959 A | 6/1990 | Horzewski et al. | |
| 4,954,126 A | 9/1990 | Wallsten | |
| 4,966,583 A | 10/1990 | Debbas | |
| 4,994,047 A | 2/1991 | Walker et al. | |
| 4,998,539 A | 3/1991 | Delsanti | |
| 5,002,557 A | 3/1991 | Hasson | |
| 5,041,093 A | 8/1991 | Chu | |
| 5,042,976 A | 8/1991 | Ishitsu et al. | |
| 5,122,122 A | 6/1992 | Allgood | |
| 5,163,949 A | 11/1992 | Bonutti | |
| 5,183,464 A | 2/1993 | Dubrul et al. | |
| 5,197,971 A | 3/1993 | Bonutti | |
| 5,295,994 A | 3/1994 | Bonutti | |
| 5,324,270 A | 6/1994 | Kayan et al. | |
| 5,331,975 A | 7/1994 | Bonutti | |
| 5,345,927 A | 9/1994 | Bonutti | |
| 5,400,773 A * | 3/1995 | Zhu et al. | 600/207 |
| 5,496,345 A * | 3/1996 | Kieturakis et al. | 606/192 |
| 5,514,091 A | 5/1996 | Yoon | |
| 5,569,183 A | 10/1996 | Kieturakis | |
| 5,653,726 A | 8/1997 | Kieturakis | |
| 5,667,520 A | 9/1997 | Bonutti | |
| 5,690,668 A | 11/1997 | Fogarty et al. | |
| 5,697,946 A * | 12/1997 | Hopper et al. | 606/185 |
| 5,722,986 A | 3/1998 | Smith et al. | |
| 5,728,119 A * | 3/1998 | Smith et al. | 606/190 |
| 5,772,680 A * | 6/1998 | Kieturakis et al. | 606/190 |
| 5,779,728 A | 7/1998 | Lunsford et al. | |
| 5,827,318 A | 10/1998 | Bonutti | |
| 5,836,961 A | 11/1998 | Kieturakis et al. | |
| 5,860,997 A | 1/1999 | Bonutti | |
| 5,865,728 A | 2/1999 | Moll et al. | |
| 6,004,337 A | 12/1999 | Kieturakis et al. | |
| 6,013,090 A | 1/2000 | Fogarty et al. | |
| 6,015,421 A | 1/2000 | Echeverry et al. | |
| 6,179,854 B1 | 1/2001 | Nash et al. | |
| 6,860,892 B1 * | 3/2005 | Tanaka et al. | 606/190 |

FOREIGN PATENT DOCUMENTS

| | | |
|---|---|---|
| SU | 1323090 | 7/1987 |

OTHER PUBLICATIONS

Hoffman et al., *Nasal Reconstruction with the Rapidly Expanded Forehead Flap*, Larynogoscope, 99: 1096-1098.

Rigg, *Inflatable Device of Intraoperative Use During Augmentation Mammaplasty*, Reconstructive Surgery, May 1982.

Cinelli et al., *The Inflatable Silastic Bag: A Practical Device that Simplifies Augmentation Mammaplasty*, From the Division of Plastic Surgery, Department of Surgery at the Maimonides Medical Center and Medical Arts Center of New York.

Sasaki, *Intraoperative Sustained Limited Expansion* (ISLE) *as in Immediate Reconstructive Technique*, Clinics in Plastic Surgery, vol. 14, No. 3, Jul 1987.

Sasaki, *Intraoperative Expansion as an Immediate Reconstructive Technique*, Facial Plastic Surgery, vol 5, No. 4, Jul. 1988.

Sanchez, *Uretropexia Laparoscopica and English Translaation*, vol. 46, No. 7, pp. 642-644, 1993.

Sanchez, *Anclaje Cervical Endoscopico. Nuevo Tratamiento para las incontinencia de Esfuerzo and English Translation*, vol. 42, No. 2, pp. 127-130, 1988.

Schmidt et al., *Continuous Versus Conventions Tissue Expansion: Experimental Verification of a Technique*, vol. 87., No. 1, pp. 10-15, Feb. 20, 1990.

(Videotape), Maxwell D 18214, Immediate Intraoperative Expansion in augmentation Mammoplasty.

Sanchez, *Uretropexia Laparoscopica Extraperitone*, Arch. Esp. de Urol. 47.4 (415-418), 1994 and English Translation.

Sanchez, Stress Incontinence: *A New Endoscopic Approach*, Urol., vol XXXVI, pp. 403-405, Nov. 5, 1990.

* cited by examiner

SPECIALLY SHAPED BALLOON DEVICE FOR USE IN SURGERY AND METHOD OF USE

CROSS REFERENCE TO RELATED APPLICATIONS

This application is a Continuation of U.S. patent application Ser. No. 09/322,201, filed on May 28, 1999, now U.S. Pat. No. 6,860,892, the disclosure of which is hereby incorporated by reference herein.

FIELD OF THE INVENTION

The field of the invention is specially shaped balloon dissection or retraction devices and their use. More particularly, the invention relates generally to an apparatus which includes a specially shaped balloon, such as a tapered balloon, and a method for dissecting and/or retracting tissue to facilitate laparoscopic procedures such as minimally invasive subfascial endoscopic perforator surgical procedures.

BACKGROUND OF THE INVENTION

More than 2.5 million people in the United States suffer from chronic venous insufficiency which includes disorders such as edema, stasis pigmentation, stasis dermatitis and stasis ulceration. Treatment of venous ulcers is difficult and costly, and their recurrence is frequent despite the treatment. Patients with venous ulcers may face partial or permanent disability and suffer the psychological and economic effects of losing mobility.

A promising approach to the treatment of chronic venous insufficiency is subfascial endoscopic perforator surgery ("SEPS"). Before discussing the SEPS procedure and the present invention's application to surgical procedures such as SEPS, it will be helpful to briefly review the venous anatomy of the leg and the pathophysiology of chronic venous insufficiency.

Venous blood is returned from the lower leg to the heart through a system comprising three types of veins: superficial veins which drain venous blood from tissue above the deep fascia in the lower leg, deep veins which drain blood from venous sinuisoids in the lower leg, and perforator veins which drain blood from the superficial veins into the deep veins.

Superficial veins include the greater saphenous vein, the lesser saphenous vein and the posterior arch vein. The lesser saphenous vein ascends from the lateral side of the foot and travels superiorly on the posterolateral side of the calf. The greater saphenous vein originates at the arch of the foot and eventually rises along the medial aspect of the lower leg. The posterior arch vein, or Leonardo's vein, drains blood from below the medial ankle, rises along the medial half of the leg and joins the greater saphenous vein.

The deep veins lie beneath the deep fascia and include the paired posterior tibial veins, the anterior tibial veins, the peroneal veins and the popliteal vein. Some of the deep veins originate at the foot and ascend the lower leg.

The perforator veins which connect the superficial veins to the deep veins are called "perforator" veins because they penetrate the deep fascia as they travel from the superficial veins to the deep veins. Perforator veins include anterior perforator veins situated on the anterolateral surface of the lower leg, lateral perforator veins found on the posterolateral surface of the lower leg, and medial perforator veins located on the medial side of the lower leg. The medial perforator veins further include the Cockett perforator veins which are located toward the ankle.

The blood pressure in veins is much lower than the blood pressure in arteries, often by a factor of fifty. The low venous blood pressure itself is incapable of returning venous blood, particularly in the lower limbs, to the heart. As a result, skeletal muscles in the lower limbs assist by contracting to pump venous blood from the lower limbs to the heart. For example, the veins in the calf muscle are surrounded by a tight muscle-fascial envelope which forms a "calf-muscle pump". Contraction of the calf muscles compresses the veins and propels the venous blood upward to the heart.

When the calf muscles are relaxed (diastolic phase), the valves of the perforator veins are open which permits blood to flow one-way from the superficial veins to the dilated soleal sinusoids of the deep vein system. The next muscle contraction (systolic phase) expels the blood temporarily stored in the soleal sinuisoids into the popliteal and femoral veins of the deep vein system. During the systolic phase of the calf-muscle pump, the valves of the perforator veins are closed to prevent blood from being expelled back through the perforator veins and into the superficial veins. The valves of the perforating veins further protect various subcutaneous tissues from the muscular systolic pressure generated by the calf-muscle pump, which pressure may range from 150 to 300 mm Hg.

When the valves in the perforator veins fail to function correctly (perforator vein incompetence), blood will flow backward (reflux) from the deep veins to the superficial veins, thereby failing to return to the heart. Perforator vein incompetence may be caused, for example, by local trauma, long-term saphenous incompetence, or minor calf-vein thrombosis.

Reflux of blood due to perforator vein incompetence may result in chronic ambulatory venous hypertension, that is, a persistent case of elevated ambulatory venous pressure. Patients with chronic ambulatory venous hypertension may have symptoms such as aching, fullness, or tiredness in their lower leg. Chronic ambulatory venous hypertension may further lead to venous ulceration, a painful and often debilitating condition. In fact, the more extensive and the more distal the reflux, the greater the chance that the patient will develop a venous ulcer.

According to one study, 80–90% of incompetent perforator vein cases involve the medial perforator veins in the lower leg, 15% involve the lateral perforator veins, and 5% involve the anterior perforator veins. Of the 80–90% of incompetent perforator vein cases which involve the medial perforator veins in the lower leg, most occur near the region of Cockett's perforator veins. Cockett's perforator veins are located at roughly six, twelve and eighteen centimeters from the heel sole.

Treatment of chronic venous insufficiency includes non-invasive treatments such as leg elevation to foster draining the blood out of the lower leg, compression by application of bandages to reduce venous pressure in the lower leg, and topical therapies to promote healing of ulcerous wounds. Treatment also may include invasive treatments such as sclerotherapy, skin grafting, stripping of superficial veins, open subfascial perforator surgery, subfascial endoscopic perforator surgery and deep vein reconstruction. The proper treatment or treatments to apply depend on the particular circumstances of the patient's venous dysfunction. Skin grafting may be used to accelerate healing of ulcerous wounds through the covering of wounds with split-skin, mesh, or pinch grafts. Skin grafting, however, does not eliminate the underlying cause of venous dysfunction. Instead, it treats the symptoms of venous dysfunction such as the ulcer. Thus, recurrence of ulcers is likely. Sclerotherapy involves injecting a sclerosing solution into, dysfunctional blood vessels to cause them to obliterate. The removal of dysfunctional vessels reduces venous reflux. Similarly, superficial vein stripping involves excising dysfunctional superficial veins by subcutaneous dissection in order to reduce venous reflux. However, the removal of superficial veins does not resolve reflux problems in the perforator veins. Deep vein reconstruction is reserved for patients whose ulcers have failed to respond to all other kinds of therapy. Deep venous reconstruction includes direct valve repair (valvuloplasty), valve transposition and valve transplantation.

Open subfascial perforator surgery involves making at least one long incision in the lower leg to gain access to the perforator veins which are then ligated or removed. When incompetent perforator veins are removed, new perforator veins begin to grow through a regeneration process. As a result, dysfunctional perforator veins are replaced by regenerated perforator veins. Open subfascial perforator surgery tends to prevent recurrent venous ulceration because this treatment attacks a root cause of perforator venous dysfunction.

However, incisions near or at the locations of diseased skin (e.g., ulcers) may result in wound complications and delayed wound healing. Thus, there is a need for a surgical procedure which uses an incision site more distant from the area of ulcerative damage and yet provides access to the underlying perforator veins.

While subfascial endoscopic perforator surgery (SEPS) is not indicated for all venous dysfunctions or for all patients, it permits surgeons to make an incision more remote from an ulcerous wound and yet gain access to perforator veins underlying the ulcer. SEPS approaches vary. Some surgeons use a one-port approach where the scope and working instruments are introduced through a single incision in the proximal calf. In the dual port approach which enhances visualization, one port is used for the scope and the other port is used for the working instruments. The space created by either the single or dual port approach may be optionally insufflated with gas, such as $CO_2$, or any other suitable fluid. The SEPS approach requires the dissection of the subfascial plane so that surgical instruments can access and ligate the dysfunctional perforator veins. Dissection of the subfascial plane may be accomplished manually with surgical instruments. Besides blunt dissection, dissection can also be performed by inserting a deflated balloon to the subfascial tissue plane and then inflating the balloon to cause dissection of tissue layers along the tissue plane. A traumatic balloon dissection of the subfascial plane exposes the perforator veins and creates space for the surgeon to access and ligate dysfunctional perforator veins, while minimizing trauma to the blood vessels, long-standing ulcers and damaged tissues. Compared to blunt dissection, balloon dissection results in less bleeding, due in part to the atraumatic nature of tissue dissection and in part to the tamponade effect of the balloon on surrounding tissues. Thus, the balloon offers the advantage of minimizing trauma to certain tissues (e.g., veins) while accomplishing sufficient dissection of tissues to afford visualization, if desired, as well as access to the vein.

The Spacemaker SEPS balloon device (model number VDB 300), which is manufactured and sold by General Surgical Innovations, Inc., the assignee of the present patent application, is a balloon device which may be used to dissect the subfascial plane for a SEPS procedure. This balloon is mounted to a cannula and inflates to a predictable cylindrical shape. The diameter of the cylindrical balloon is generally uniform along the length of the balloon.

Because many of the incompetent perforator veins occur near the ankle where blood is the furthest from the heart, resulting tissue damage and venous ulcers may occur near the ankle. Thus, there is a need for an improved balloon dissection device which further minimizes trauma to the already deteriorated tissue and which permits further dissection of the subfascial space at a location close to the ankle.

SUMMARY OF THE INVENTION

The present invention comprises a balloon suitable for tissue dissection and/or tissue retraction, which balloon inflates to a shape and size specially designed for the surgical procedure to be performed and the anatomy of the region of the body in which the surgical procedure is to be performed, and its method of use. A preferred use for the present balloon device is in the field of fiber optic surgery, including endoscopy, arthroscopy and laparoscopy which require looking into and operating within a limited space with a fiber optic light and camera.

A first, separate aspect of the present invention is a medical device having a balloon which inflates to a predetermined size and shape for dissecting tissue layers for the purpose of conducting a desired surgical procedure.

A second, separate aspect of the present invention is a medical device having a balloon which inflates to a tapered shape for dissecting tissue layers near the ankle in a SEPS procedure.

A third, separate aspect of the present invention is a medical device having a balloon which has a non-tapered portion and a tapered portion where inflation of the balloon dissects tissue layers in a SEPS procedure.

A fourth, separate aspect of the present invention is a medical balloon device whose balloon is shaped upon inflation to dissect tissue in a non-uniform manner. For example, the balloon may be shaped such that each portion of the balloon causes a different amount of dissection of the surrounding tissues. Besides affecting the amount of dissection, the balloon also may be shaped to cause variations in the location, shape, direction, or any other characteristic of the resulting dissection.

A fifth, separate aspect of the present invention is a medical balloon device whose balloon is inverted or gathered about a cannula.

A sixth, separate aspect of the present invention is a medical balloon device whose balloon is inverted or gathered about a cannula and inflates in stages such that the balloon unfolds, everts and inflates (but not necessarily in that order).

A seventh, separate aspect of the present invention is a medical balloon device whose balloon is inverted and whose cross section is sized to assure sequential inflation of the balloon after the main body of the balloon is inflated.

A eighth, separate aspect of the present invention is a medical balloon device whose balloon unfolds, everts and/or inflates in a controlled, predetermined manner.

An ninth, separate aspect of the present invention is a medical balloon device having a handle comprising a plurality of sections where each section is used to remove a respective part of the device from inside the patient's body. After using the plurality of sections to remove parts of the device from the patient's body, a port providing access into the patient's body remains.

A tenth, separate aspect of the present invention are balloon dissection methods for dissecting tissue to provide access to an anatomical structure inside the patient's body.

BRIEF DESCRIPTION OF THE DRAWINGS

Reference is made to the accompanying drawings, where like reference numerals are used on like parts and where illustrative embodiments of the invention are shown from which one of ordinary skill in the art will appreciate novel features and advantages of the present invention.

DETAILED DESCRIPTION OF THE PREFERRED EMBODIMENTS

The balloon devices described and claimed herein are suitable for the various uses disclosed in the parent and other applications which have been incorporated herein by reference.

The balloon dissection device as described herein may utilize an elongate balloon with a tunneling shaft assembly of the types described in any one of U.S. patent application Ser. No. 07/893,988, U.S. Pat. No. 5,836,961 (Ser. No. 08/124,283), U.S. Pat. No. 5,607,443 (Ser. No. 08/267,488), U.S. Pat. No. 5,730,756 (Ser. No. 08/388,233), U.S. Pat. No. 5,772,680 (Ser. No. 08/570,766) and U.S. Pat. No. 5,540,711, the disclosure of each of which is assigned to General Surgical Innovations, Inc., the assignee of the present patent application, and the entirety of which is hereby incorporated by reference in its entirety. U.S. Pat. No. 4,271,839 to Fogarty et al. which discloses a balloon catheter with an inverted balloon and the entirety of which is also expressly incorporated by reference herein. Similarly, U.S. Pat. Nos. 5,690,668 and 5,601,589, both by Fogarty et al., are also expressly incorporated by reference herein.

Figure 1:
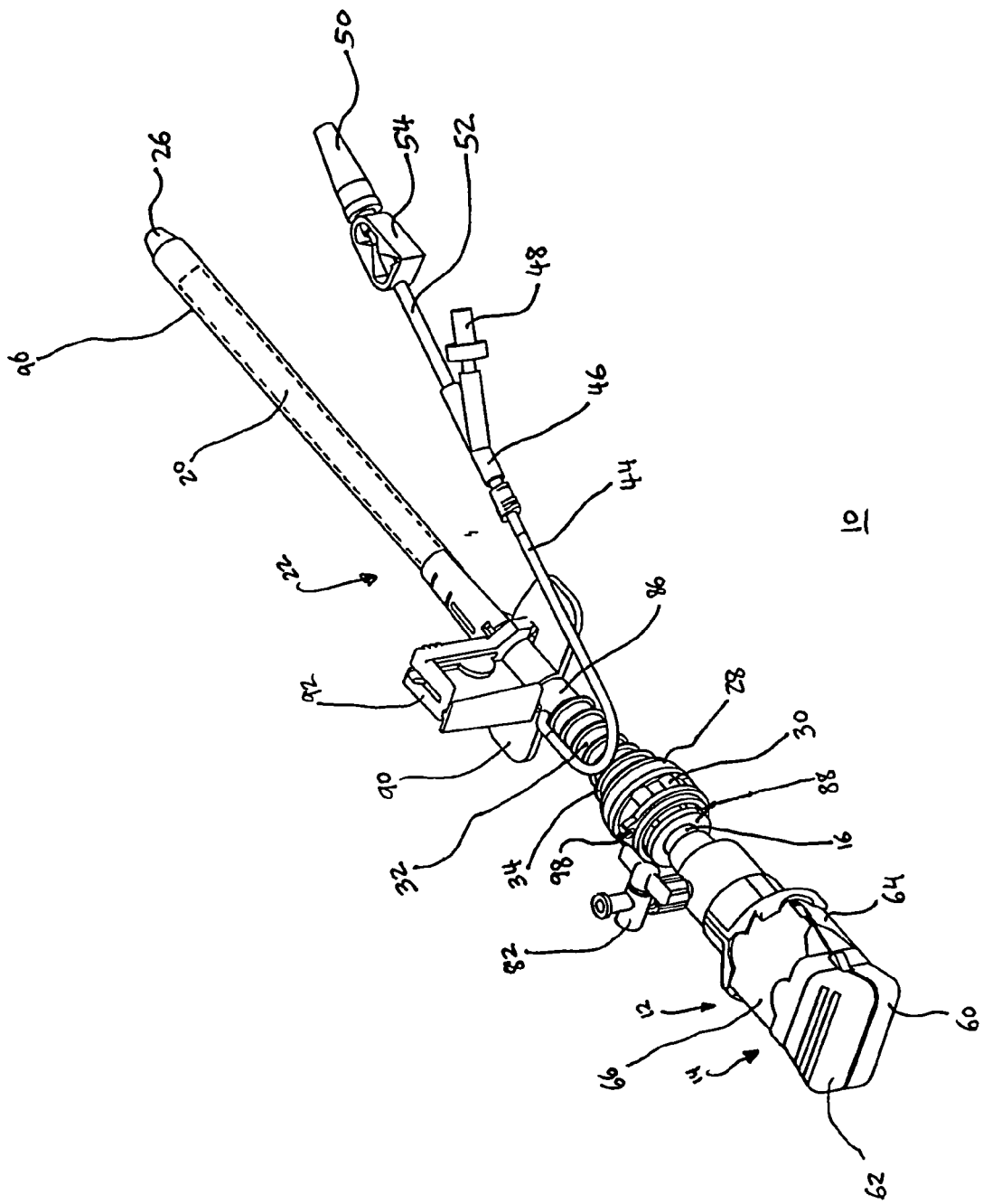
FIG. 1 is a perspective view of an embodiment of the invention prior to insertion of the device into a patient.

With traditional blunt dissection, the incision in the skin must be larger than the surgical area being worked upon, so that the surgeon can insert and move the mechanical dissectors and instruments into position. By contrast, the balloon dissection device of the present invention, an exemplary embodiment of which is illustrated in FIG. 1, is insertable through a small laparoscopic incision. With the balloon dissection device 10, the opening at the skin is smaller at the skin where the device is inserted and wider at the location inside the body where the balloon is expanded. The balloon 20 is first placed into the body in a deflated state, and then, as it is inflated, the balloon dissects and pushes tissue out of the way in the deeper layers of the body so that one can see and safely operate on affected tissue. Inflation of the balloon 20 dissects and moves appropriate tissue out of the way to enable a surgeon to see and work better within the body. The balloon 20 may also be used to dissect and move tissue in order to create a space between the tissues for visualization and/or for working. The balloon 20 can be left inflated in the tissue while the surgeon inserts working and/or visualization instruments and performs a surgical procedure outside the balloon 20. Alternatively, the balloon 20 can be deflated and removed prior to the insertion of instruments and the performance of the surgical procedure.

As shown in FIG. 1, the balloon dissection device 10 includes a tunneling shaft assembly 12 substantially similar to the tunneling shaft assembly disclosed in U.S. Pat. No. 5,690,668. The tunneling shaft assembly 12 has a multiple-piece handle assembly 14. Alternatively, a hollow tube having either a one or two-piece handle construction as disclosed in U.S. patent application Ser. No. 08/570,766 may be utilized. The handle assembly 14 includes a cannula 16, a tunneling shaft 18 and an obturator 24. The tunneling shaft 18 extends through a bore in the obturator 24. The obturator 24 extends through the cannula 16. The tunneling shaft 18 may have an olive-shaped, or other blunt-shaped, obturator 26 mounted on its distal end to provide a blunt distal end for tunneling.

A skin seal 28 may be utilized if needed for the procedure to be performed, and may be as substantially described in U.S. Pat. No. 5,836,961 (Ser. No. 08/124,283). The skin seal 28 may be slidably mounted and frictionally retained on the outer surface of the cannula 16. A movable collar 30 on the skin seal 28 provides for adjustment on and locking to the outer surface of the cannula 16. The outer surface 32 of the skin seal 28 is progressively cylindrical and tapered and has helical screw threads 34 for engaging the skin of the patient to form an air-tight seal with the skin.

Figure 2:
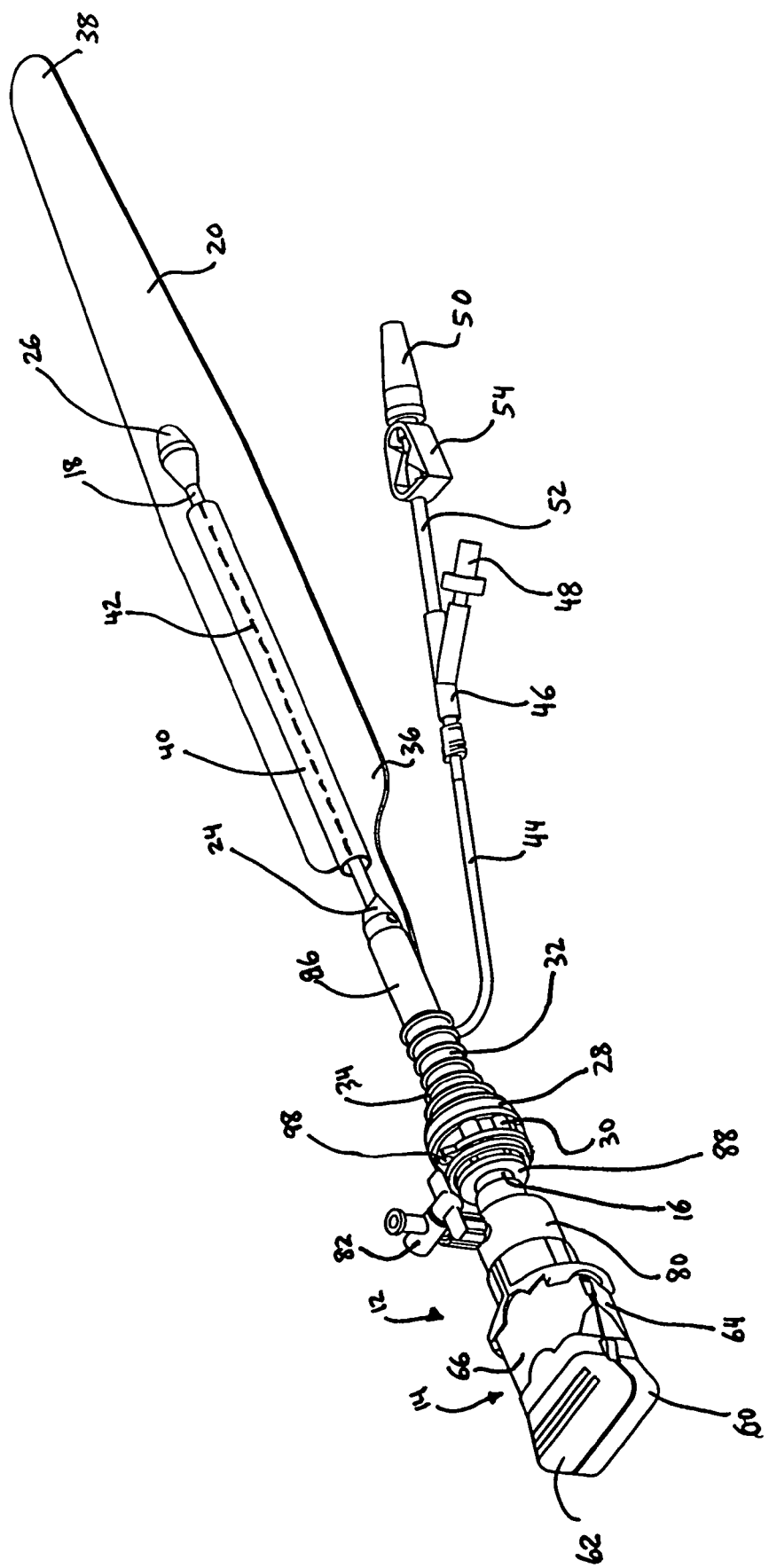
FIG. 2 is a perspective view of the embodiment of FIG. 1 where the balloon cover has been removed and the balloon unfolded.
Figure 3:
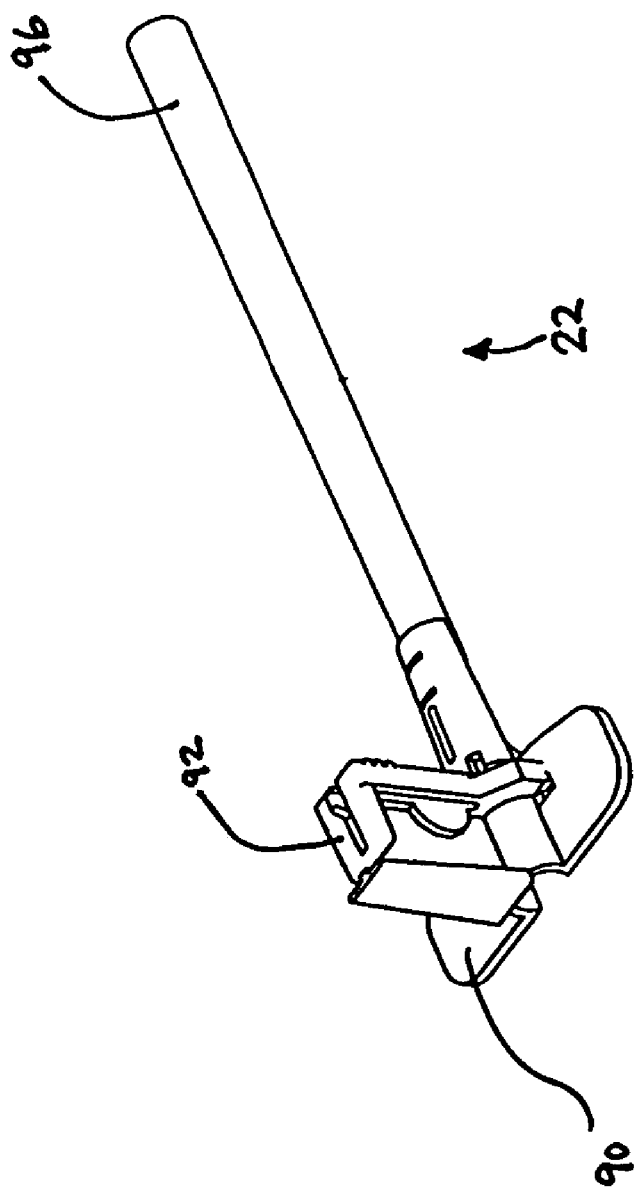
FIG. 3 is a perspective view of the balloon cover of the embodiment shown in FIG. 1.
Figure 4:
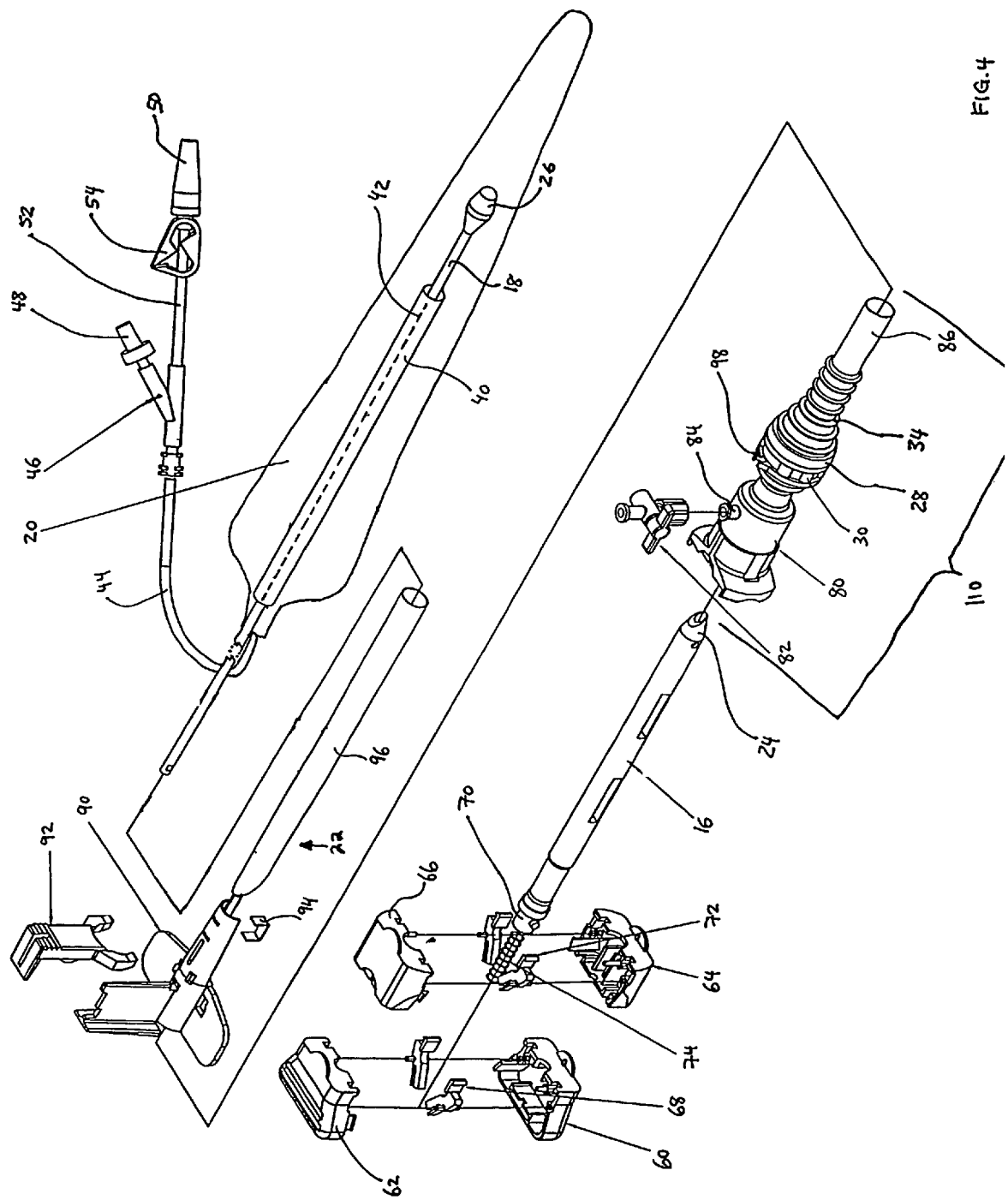
FIG. 4 is an exploded view of the parts of the embodiment of FIG. 1.
Figure 5:
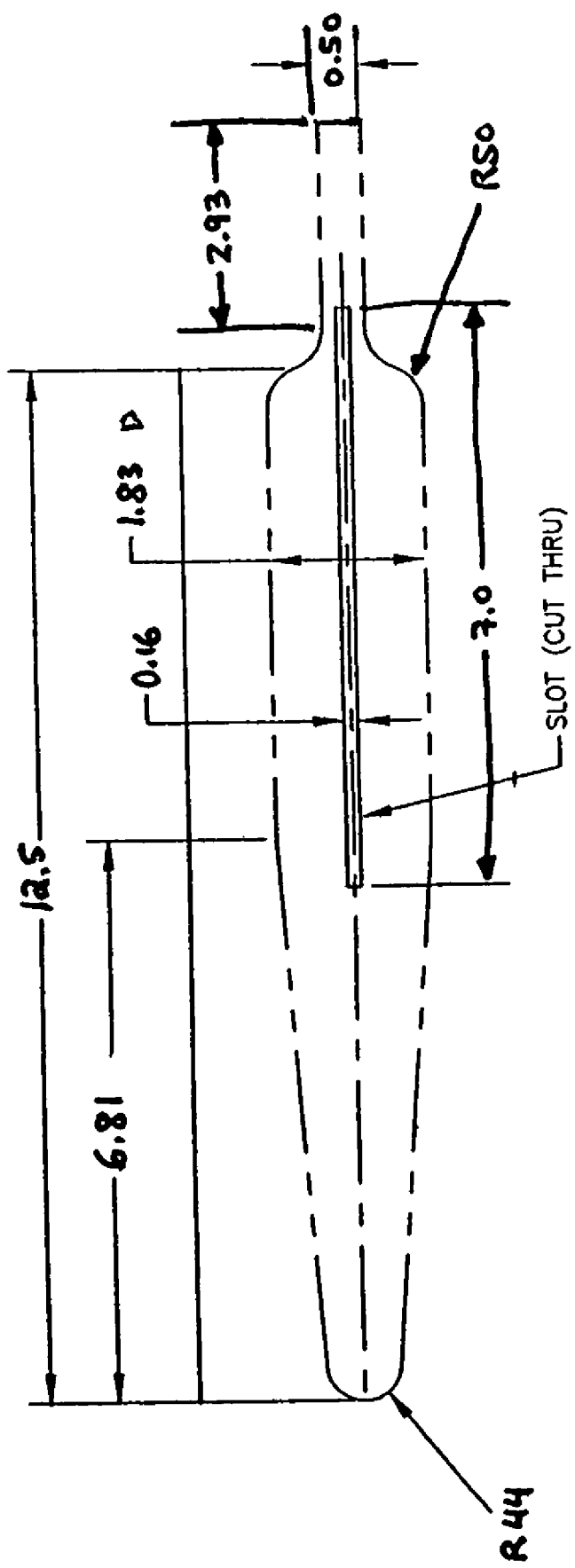
FIG. 5 shows the dimensions of a preferred embodiment of a 240 cc tapered balloon for a SEPS procedure.

Prior to inflation, the balloon 20 would appear as shown in FIGS. 1 and 5. In FIG. 1, the balloon 20 is shown in dotted lines under a balloon cover 22. FIG. 2 depicts the balloon dissection device of FIG. 1 with the balloon cover 22 removed and the balloon 20 in its unfolded (deflated) state. FIG. 3 illustrates the balloon cover 22 of FIG. 1 after removal. FIG. 4 is an exploded parts view of the balloon dissection device of FIG. 1. FIG. 5 depicts the dimensions in inches of a preferred embodiment of a 240 cc tapered balloon which may be used for a SEPS procedure.

As shown in FIGS. 1–4, an inflatable elongate balloon 20 is mounted on the tunneling shaft 18 which is part of the tunneling shaft assembly 12. The tunneling shaft 18 may be a type of cannula to receive an endoscope, or rod. The balloon 20 has a proximal end 36 which is closest to the handle 13 and a distal end 38 which extends substantially beyond the distal-most point of the tunneling shaft 18 when the balloon is fully inflated. The balloon 20 can be mounted on one side of a cannula or a scope, or it can be mounted to surround the cannula or scope. The balloon 20 also can be mounted on a separate shaft passing through a lumen or channel of the cannula. The shaft with a balloon on the end can be pushed or slid through the cannula. Alternatively, the balloon 20 can expand out of, then recess back into, a groove on a cannula. The balloon 20 and/or the cannula to which it is mounted can have multiple lumens through which other instruments may be passed. The cannula may have multiple balloons, each of which may be independently controlled or inflated to, for example, dissect tissue layers in stages. Alternatively, the multiple balloons may be controlled as a single unit.

Figure 11:
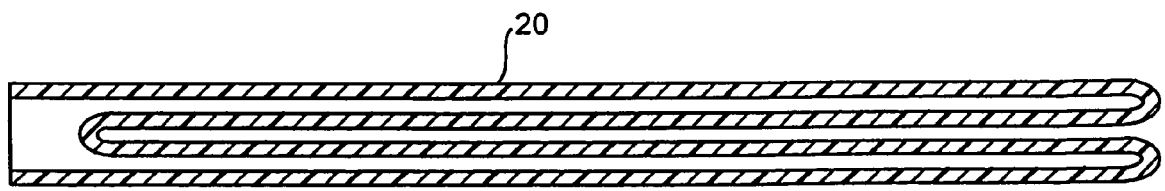
FIG. 11 is a cross section view of a balloon that has been everted into itself.

The improved balloon device provides for an inflatable balloon which optionally may be inverted, folded, or rolled about a tunneling shaft 18. In a preferred embodiment, the deflated, elongate balloon 20 has at least part of its distal extremity folded inwardly to shorten its predeployment length. FIG. 11 illustrates a cross-section view of a balloon which has been inverted into itself. The distal portion 38 of the balloon 20 can be folded inwardly by, for example, inverting the distal end portion 38 of the balloon 20 into the proximal portion 36 so that approximately one-half of the balloon 20 is folded into the other half of the balloon 20, reducing its overall length when deflated to approximately one-half of its fully extended, inflated length. This prevents the distal portion 38 of the folded balloon 20 from extending substantially beyond the distal extremity of the tunneling shaft 18. If a shorter folded balloon 20 is desired, the balloon 20 may be shortened further by repeatedly inverting and/or folding the portion of the balloon 20 which is now the most distal point of the balloon so that the inflated balloon 20 is, for example, reduced to be approximately one-fourth of its fully extended, inflated length. Additional inversions and/or folds are possible. Moreover, each fold need not be to shorten the balloon by one-half, but a fold can reduce the length of the balloon 20 by some other amount. Moreover, the balloon 20 can be folded lengthwise any number of times toward the tunneling shaft 18, or be rolled or gathered about the tunneling shaft 18, in order to reduce the width of the balloon 20. Diagonal folds are also possible.

Thus, as the balloon 20 is inflated, the balloon 20 progressively unwraps itself from the tunneling shaft 18 as its side margins move outwardly from the center axis of the balloon while expanding to cause progressive separation or dissection of tissue by the application of forces generally perpendicular to the surface of the balloon 20. If inverted, the cross-sectional aspect of the balloon may be sized to assure sequential inflation after the main body of the balloon is inflated. In this manner, the main body of the balloon can be made to act as an anchor from which the inverted balloon may extend distally in a controlled manner, increasing the dissection.

The balloon 20 is flexible and has no significant sharp edges which might injure tissue being moved or dissected by the balloon. The balloon 20 may be made of a stretchable material which stretches when pressurized from within so as to conform, to the extent desired, to the surrounding tissue confines and then collapses partially of its own accord when depressurized or with the help of suction. For example, the balloon 20 may be made of an elastomeric material such as Silastic elastomer which is available from Dow Corning in medical grades. Other suitable materials include silicone, latex, or polyvinylchloride (PVC).

Alternatively, the balloon 20 may be of a more inelastic material which does not stretch significantly, but which expands when pressurized from within and which may be collapsed by the use of suction. In this case, it would preferably be made of a polymer of the class including Kevlar or Mylar film for strength and structural integrity. Generally, the balloon also may be made from any very thin walled polymer.

In the preferred embodiment for a SEPS procedure, the balloon 20 inflates to a generally predetermined size and shape by methods and materials as known to those of skill in the art. Balloon 20 is preferably formed of a non-elastomeric, medical grade material of a suitable type such as polyvinyl chloride, polyethylene, or polyurethane. For example, a suitable material for the balloon 20 which is to be used in a SEPS procedure is 0.006 inch thick polyurethane film such as PS-8010 supplied by Deerfield Urethane, Inc. of South Deerfield, Mass. Balloon 20 can be formed of two sheets of such material which have their outer margins bonded together by suitable means such as by adhesive or heat at a margin extending around the perimeter of the balloon. Alternatively, balloon 20 may be formed out of a single formed or molded piece.

The balloon 20 may also be made from a biocompatible and/or biodegradable material so that if the surgeon desires to keep the balloon 20 in place in the body for a extended period of time, it will not harm the tissue. The balloon 20 can be made of a composite material, that is, a particle or fiber-reinforced material. Composite materials can be made to be strong while flexible. Composite materials also allow the balloon to assume a specific shape upon inflation. The composite material may also be biodegradable if desired.

The surface of the material of the balloon 20 can be pebbled, roughened, or ridged, or have serrated edges, to better grip tissue and hold the balloon 20 in position. The balloon 20 also may be made of a transparent material to provide the surgeon with a better visualization of the operating area. One surface of the balloon 20 may be made of or have thereon a reflective surface to reflect light if desired.

The balloon 20 optionally may be reinforced with stainless steel, nylon, or other fiber to prevent puncturing and to provide structural shape and support. The balloon may have an inner and outer wall such that filaments, tethers, or cords are placed between the inner and outer walls to limit their separation from each other. For further detail about such embodiments, see U.S. Pat. No. 5,514,153 and U.S. Pat. No. 5,331,975, which are assigned to General Surgical Innovations, Inc., the entirety of each of which is incorporated herein by reference. The inner wall can be made more rigid than the outer wall. The balloon also may include one or more stretchable (inflatable or expandable) parts and one or more non-stretchable parts. The non-stretchable parts can be metal or plastic pieces such as curved plates which are joined by the stretchable elements which extend longitudinally between them.

The balloon may inflate to any suitable size or shape. For example, if the surgeon is working against bone, he can select a balloon which is configured to lie flat against the bone and expand away from the bone in order to push tissue away from the bone. As a further example, in the preferred embodiment for a SEPS procedure, the balloon may be continuously tapered as illustrated in FIG. 1, or have a cylindrical, non-tapered body portion and a tapered end portion as depicted in FIG. 5. FIG. 5 shows the preferred dimensions in inches of a 240 cc balloon 20. There are numerous ways to control the size and shape to which the balloon inflates.

For example, for a common material, upon application of a given amount of force, a thinner material will stretch more than a thicker material. Thus, all other factors being equal, an inflatable device will stretch more where it is thinner and will stretch less where it is thicker. This is one way to control the shape into which a balloon expands when it is inflated. As an example, if a balloon has one half made of a very thick material and one half made of the same but much thinner material, the thin material will stretch more quickly and easily and the balloon will expand unevenly. The thin half of the balloon will expand more than the thicker material under the same pressure. The rate of expansion of different portions of the balloon may be controlled by using different materials or different thicknesses of materials. For example, if the balloon has portions formed of a thicker material and portions formed of a thinner material, the thinner portions will expand before the thicker portions expand. Consequently, tissue may be dissected in stages, or selectively as needed.

A second way to control the shape of expansion of the balloon is to use a fiber reinforced material. The direction of the fibers, along with their number, spacing, layering and length, controls the rate of expansion of the matrix material. Also, areas devoid of fibers will expand faster and/or further than areas which are reinforced. Specifically, the fibers resist stretching along their length. Thus, the balloon will stretch more in a direction across the fibers, or where the fibers are not present, than in a direction along the fibers. Fibers can be placed at the edge of the balloon to maintain the shape of the balloon when inflated. Fibers can be layered, with one layer in one direction and another layer in another direction, to control expansion in more than one direction. Adding fibers may make the balloon more puncture and tear resistant. For this purpose, the balloon can also be made of or include a self-sealing material.

A third way to control the shape of the balloon after inflation is to pre-shape the balloon to assume a certain form when expanded. This may be done in a molding process or example, the balloon may be formed on a mandrel which is of a particular shape and which is sized about half way between the unexpanded and the desired expanded size of the balloon.

Another way to achieve shape control is to fix tethering cords to portions of the balloon in order to control and/or limit the expansion of the balloon. Yet another way is to add a plate which limits the shape of the balloon. For example, if a flat plate is added to a portion of the surface of the balloon, the flat plate will remain flat and result in a flat area on one side of the balloon when inflated. The balloon can have multiple such plates to create specific shapes.

Accordingly, the balloon 20 itself can be round, eccentric, oval, conical, wedge-shaped, U-shaped, curved, angled, or it may be in any shape desired for the particular application. The balloon 20 may be irregularly shaped when inflated such that it expands more in an area where the surgeon desires to have more visualization (where greater operating space is needed). Since skin expands from an incision in an elliptical fashion, the balloon can be made to assume such an elliptical shape to fit into the natural opening and cause less trauma. For further detail about the various types of balloons, balloon materials, balloon sizes and balloon shapes which may be used, see U.S. Pat. Nos. 5,514,153 and 5,331,975.

In order to inflate the balloon 20, a flexible tubular member 44 may be utilized as an inflation lumen for the balloon 20. Balloon 20 has a neck into which one end of the tubular member 44 extends. The tubular member 44 may be secured to balloon 20 in a suitable airtight fashion, such as by an adhesive. One end of the tubular member 44 passes and opens into the interior space of the balloon 20 so that an inflation fluid can be introduced or withdrawn from the balloon 20. The other end of the tubular member 44 is connected to a wye adapter 46. A hand-operated syringe (not illustrated) may be connected to an extension 48 of the wye adapter 46 as shown in FIG. I and utilized to inflate the balloon 20 with a suitable fluid. Suitable fluids include, for example, air, water, dextrose water, normal saline, $CO_2$, $N_2$ and other fluids. Optionally, a check valve may be used to prevent deflation of the balloon if the syringe or other pressure source is disconnected. The pressure in the balloon 20 may be monitored and regulated to keep the force exerted by the retractor at a safe level to prevent tissue necrosis and/or damage. The wye adapter 46 is also connected to a male evacuation fitting 50 by tube 52 which has a pinch clamp 54 mounted thereon. The evacuation fitting 50 terminates the tube 52 and may be connected to a wall suction device or aspirator (not shown) to evacuate the fluid from the balloon 20 when one wants to deflate the balloon. The body of the tubular member 44 may be attached to a notch 98 on the skin seal assembly 28 so as to prevent the tubular member 44 from getting in the way of the surgeon.

The balloon 20 is releasably secured to the tunneling shaft 18 by a sleeve 40, as best shown in FIG. 2. The sleeve 40 can be formed from the same material as the balloon 20 and may be formed as an integral part of the balloon 20 by bonding the balloon material together. Alternatively, the sleeve 40 may be formed as a separate member of the balloon 20 and for example, bonded to the balloon 20 by welding, heat sealing, or through the use of a suitable adhesive. The sleeve 40 extends along a substantial length of the balloon 20 and is typically, but not necessarily, disposed generally equidistant from the side margins of the balloon 20. The sleeve 40 is provided with a passage extending therethrough which is sized to slidably accommodate the tunneling shaft 18. The balloon 20 may be separated from the tunneling shaft 18 through the use of, for example, a weakened wall region 42 in and extending along the sleeve 40. The weakened region 42 may be formed by the co-linear, longitudinally spaced apart perforations 42 which are spaced closely enough together to form a weakened region 42. The weakened region 42 permits the balloon 20 and the sleeve 40 to be readily separated from the tunneling shaft 18 as desired. The distal portion of the sleeve 40 can be provided with means, e.g., a radially extending ridge (not shown), which will create a tighter fit with the tunneling shaft 18 and inhibit inadvertent axial movement of the balloon 20 on the shaft 18.

In a preferred embodiment, the side margins of the deflated balloon 20 is gathered about the tunneling shaft 18. Suitable methods of gathering the balloon about the shaft 18 include wrapping the balloon 20 around the tunneling shaft 18, rolling the side margins of the balloon 20 towards the tunneling shaft 18 and rolling the balloon 20 around the shaft 18. When in a gathered configuration, balloon 20 can be enclosed within a removable balloon cover 22 which comprises a cylindrical tube as shown, e.g., in application Ser. No. 08/717,794, filed Sep. 20, 1996, which is incorporated herein by reference. The removable balloon cover 22 surrounds, at least substantially, the balloon 20. The deflated balloon is shown in dotted lines in FIG. 1 since it lies under the removable balloon cover 22. The balloon cover 22 protects the deflated balloon 20 as the device is being inserted into a patient. The removable balloon cover 22 is assembled as follows. As shown in FIG. 4, the removable balloon cover 22 includes a balloon cover handle 90. A release lever 92 is attached to the balloon cover handle 90. The balloon cover handle 90 is attached by a staple 94 to a balloon cover tube 96. In FIGS. 1, 3 and 4, a removable balloon cover 22 of the type described in U.S. patent application Ser. Nos. 07/893,988 or 08/124,283 may be utilized in connection with the balloon dissection device 10 disclosed herein. The balloon cover 22 encloses the deflated balloon 20 and holds it against the tunneling shaft 18. The removable balloon cover 22 serves to frictionally retain the collapsed balloon 20 about the tunneling shaft 18. The balloon cover 22 may have a slit extending along the length of the balloon cover 22 to permit the cover 22 to be separated from the balloon 20 and the tunneling shaft 18. Instead of having a slit, the removable balloon cover 22 may have a weakened region such as perforations extending along the length of balloon cover 22.

Alternatively, a balloon cover which is integrally formed with the balloon 20 of the type described in U.S. patent application Ser. No. 08/267,488 and/or U.S. patent application Ser. No. 08/570,766, for example, may be used with the balloon dissection device 10 in lieu of the removable balloon cover 22. Such an integral balloon cover may be provided with a weakened region extending along its length so that the balloon cover separates from the balloon 20 in the tunneling shaft 18 as the balloon 20 is inflated. Alternatively, the balloon 20 can be packed into the balloon cover 22 without the presence of a tunneling guide shaft 18.

Squeezing the release lever 92 towards the vertical extension of the balloon cover handle 90 separates the balloon cover tube 96 from the balloon 20 and the tunneling shaft 18. If the balloon cover tube 96 has a slit, the balloon 20 and tunneling shaft 18 would pass through the slit. If the balloon cover tube 96 has perforations, or is similarly weakened, squeezing the release lever 92 causes the balloon cover tube 96 to lift upward whereupon the force causes the perforations to break, freeing the tube 96 from the balloon 20 and the tunneling shaft 18.

The construction of an embodiment of the balloon dissection device is shown in FIG. 4. The handle assembly 14 comprises a tunneling shaft handle portion comprised of a first end half 60 and a second end half 62, and a cannula handle portion comprised of a first center half 64 and a second center half 66. The first end half 60 and second end half 62 are secured to the proximal end of the tunneling shaft 18 to form the tunneling shaft portion of the handle assembly 14. The movable latches 68 are held in place by the first end half 60 and the second end half 62.

Similarly, the first center half 64 and second center half 66 are secured to the proximal end portion 70 of the cannula 16 to form the cannula handle portion of the handle 14. The movable latches 72 are held in place by the first center half 64 and the second center half 66. The movable latches 68 couple the tunneling handle portion to the cannula handle portion of the handle assembly 14. By depressing a portion of the movable latches 68 which protrudes to the exterior of the handle assembly 14, the latches 68 move to release the tunneling shaft handle portion from the cannula handle portion. Once released, the surgeon can move the tunneling shaft 18 along its longitudinal axis by pulling on the tunneling shaft handle portion. Pulling the tunneling shaft handle portion away from the incision in the patient causes the tunneling shaft 18 to compress a compression spring 74. The compression spring 74 lies between the end of the cannula 16 and the cannula handle portion of the handle assembly 14. The compression of compression spring 74 depresses latches 72, which releases the cannula handle portion (reference numerals 64, 66) from the trocar assembly section 110.

The latches 72 releasably couple the cannula handle portion of the handle assembly 14 to the trocar assembly 80. The cannula 16 and its obturator 24 slide into a center opening of a rubber seal 88 and then through a center opening in the trocar assembly 80. One side of the rubber seal 88 is inserted into the center opening of the trocar assembly 80, while the other side of the rubber seal 88 does not abut any other structure. The trocar assembly 80 has an integrally formed tubular extension 84 to which a stopcock 82 is mounted. The stopcock 82 permits the introduction of any suitable insufflation fluid into the dissected space in the body tissue. The trocar assembly 80 further includes a tube 86 on which the skin seal assembly 28 is mounted. The skin seal assembly 28 includes a movable collar 30 which can slide along the skin seal assembly 28 in a direction parallel to the longitudinal axis of the tube 86. When the skin seal assembly 28 is inserted into a patient's body, the rubber seal 88 remains on the exterior of the body and serves-to isolate the interior of the patient's body from the external air. The cannula 16 and the obturator 24 slide into a center opening of the tube 86 and protrude from the end of the tube 86, as illustrated in FIG. 1.

The operation and use of the balloon dissection device 10 will now be described in connection with an exemplary surgical procedure. SEPS is one example of a procedure where the present balloon dissection device 10 may be used. In the SEPS procedure, it is desirable to obtain access to a diseased or malfunctioning vein in a patient's leg so that the surgeon can ligate, divide and/or remove the diseased vein. Ligation and/or removal of such diseased veins, including the perforator veins, has been known to be an effective treatment of chronic venous insufficiency. While the entire surgical treatment procedure such as SEPS is a surgical procedure, each subprocedure such as ligation or division is also considered to be a surgical procedure.

In a preferred method of using the improved balloon device to ligate incompetent perforating veins in a SEPS procedure, the surgeon performs the following steps. First, the surgeon makes an incision 128 of about 10–15 millimeters over the medial aspect of the superficial posterior compartment of the lower leg. The surgeon performs blunt dissection with narrow blade retractors (e.g., Army Navy type) until the surgeon can easily identify the fascia in the leg. An incision of approximately one centimeter is made in the fascia so the surgeon can visualize the muscle. The surgeon inserts the blade of the narrow blade retractor under the fascia inferiorly to develop the subfascial plane.

Figure 6:
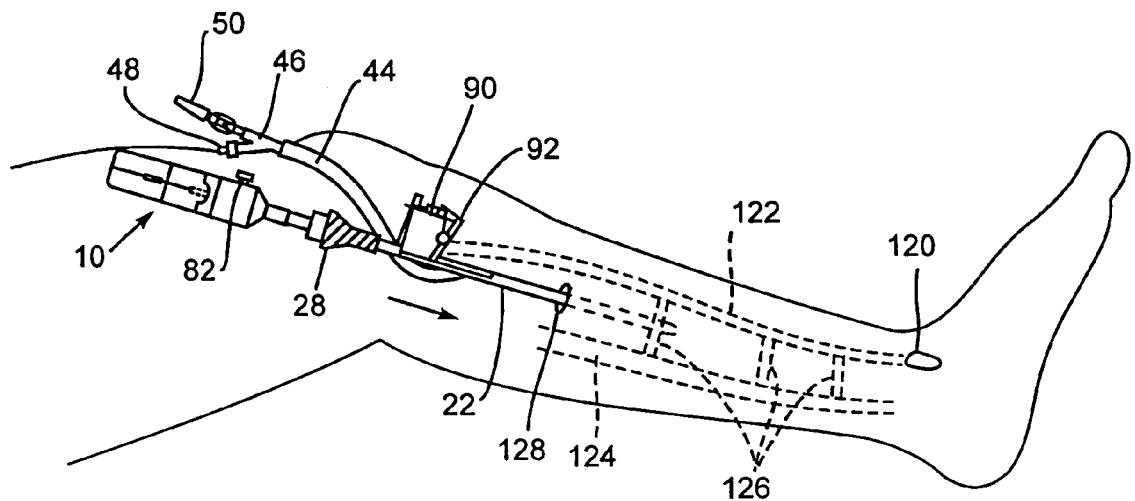
FIG. 6 is a schematic diagram which illustrates the insertion of an embodiment of the balloon dissection device of the present invention into the lower leg of a patient for a SEPS procedure.

FIG. 6 illustrates a patient's lower leg, a venous ulcer 120 located near the patient's ankle, the superficial vein 122, the deep vein 124 and the connecting perforator veins 126. As shown in FIG. 6, the balloon dissection device 10 which has a deflated and folded elongate balloon 20 covered by the removable balloon cover 22 is inserted into the incision 128 into the subfacial plane and placed adjacent an elongate structure aided by a laparoscope, a finger, or other tunneling member. For example, an elongate structure may include, but is not limited to, a blood vessel, vein, artery, nerve, bone, muscle, tissue plane, or any other elongate structure. The deflated and folded balloon 20 is then optionally bluntly advanced alongside the elongate structure until it reaches a region where it is desired to dissect tissue. For example, to facilitate a SEPS procedure, the deflated balloon 20 may be advanced to the subfascial plane near the vein or veins such as the perforator veins to be ligated and divided in the lower leg of a patient. As the balloon is advanced alongside the elongate structure in the subfascial plane, a laparoscope may be utilized to observe beyond the distal end of the balloon, either from within or alongside the balloon. It is preferable that the balloon dissection device 10 be advanced inferiorly until the balloon cover tube 96 lies almost completely within the subfascial plane.

Figure 7:
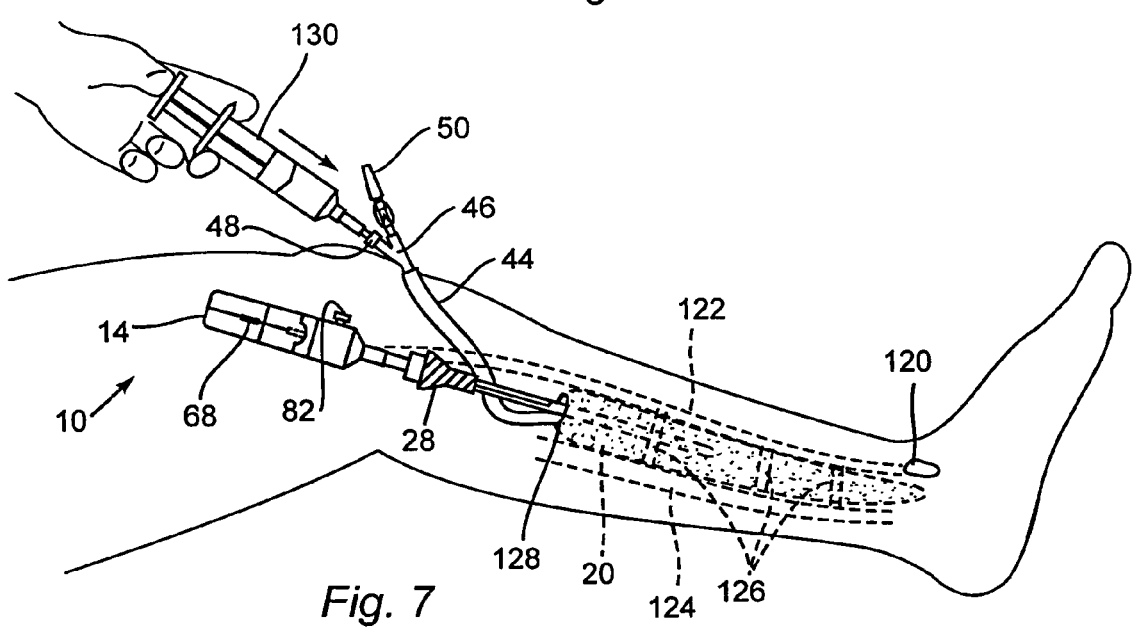
FIG. 7 is a schematic diagram which illustrates the inflation of the balloon after insertion of the device of FIG. 6 into the patient's lower leg.

The balloon cover 22 is removed by depressing the release lever 92 on the balloon cover handle 90. Upon release of the balloon cover 22, the surgeon withdraws the balloon cover 22 from the patient's leg through the incision. By using a syringe 130 connected to an extension 48 of the wye adapter 46, the surgeon pumps any suitable inflation fluid through tube 44 and into the deflated balloon 20. At this time, the skin seal assembly 28 is not yet in engagement with the incision 28. As shown in FIG. 7, introduction of the inflation fluid into the balloon 20 causes the balloon 20 to inflate in stages to the desired fill volume (e.g., about 300 cc). At first, the balloon 20 inflates laterally and then when inflated sufficiently, it begins to evert longitudinally. As the balloon 20 inflates laterally and longitudinally, the inflating balloon 20 exerts force on surrounding tissue layers which dissects the tissue layers along a natural tissue plane. Inflation of the balloon 20 may dissect the tissue to create a space within the tissue. This space may be occupied in part or in whole by the inflated balloon 20. The balloon 20 may dissect one type of tissue from another type of tissue (e.g., vein tissue from fatty tissue) as well as dissect the same tissue from itself (e.g., muscular tissue from muscular tissue, or fatty tissue globules from fatty tissue globules). Depending on the length of the patient's leg, the balloon 20 need not evert fully. A laparoscope, if used, may be used to observe dissection as the balloon 20 inflates.

The tapered balloon allows the balloon to evert further distally into the lower leg and closer to the ankle where the anatomy narrows than a non-tapered balloon. An operating space closer to the ankle assists in a SEPS procedure since there is a great likelihood of weakened or diseased tissue near the ankle. Likewise, because the proximal end of the balloon 20 has a larger diameter than the distal end, inflation of the proximal end may cause more dissection in the upper part of the leg than in the lower part of the leg. This non-uniform dissection of tissue may be useful for having non-uniform space to manipulate instruments which are later inserted into that space. The elongated tapered shape of the balloon 20 allows the balloon to dissect a larger space higher in the leg but allows it to evert further distally so that the balloon 20 can reach the situs of the ankle.

Instead of having a continuously tapered shape, the balloon may have a non-tapered body portion and a tapered end portion. The precise dimensions of the tapered portion and the non-tapered portion of the balloon may be selected out of those dimensions which are suitable for the specific surgical procedure to be performed and/or the specific anatomy of the patient for which the surgical procedure is to be performed. The dimensions of a preferred embodiment of a 240 cc balloon for a SEPS procedure are shown in FIG. 5 which depicts the dimensions in inches and the radii in hundredths of inches (e.g., R44 and R50 indicate a radius of 0.44 inches and 0.50 inches respectively).

To further dissect the tissue plane, the surgeon may choose to leave the inflated balloon 20 in place between the tissue layers for a certain amount of time (e.g., a few extra minutes or longer as desired) so that the continued exertion of force by the inflated balloon on the surrounding tissues over time causes dissection beyond the immediate dissection caused by inflation of the balloon. Optionally, the surgeon can manually move the inflated balloon 20, such as in a side-to-side or back and forth motion, within the tissue layers in order to cause further dissection.

Once sufficient space has been dissected by the balloon 20, it is preferable that the balloon be deflated and removed prior to performing a SEPS procedure. However, depending on the procedure, it is possible to leave the balloon, whether inflated or deflated, within the dissected tissue layers while the surgeon performs a procedure within the dissected space.

To deflate the balloon 20, the surgeon applies suction force through the male evacuation fitting 50 to remove the inflation fluid from the balloon. To remove the now-deflated balloon from the incision, the surgeon simply pulls on the tubular member 44. Depending on the shape of the balloon, the inflation of the balloon may cause part of the weakened region 42 of the sleeve 40 to break so as to partly release the balloon from the tunneling shaft 18. However, in the preferred embodiment for a SEPS procedure, the balloon 20 is elongated and tapered so that inflation of the balloon does not tear the balloon away from the tunneling shaft 18. Instead, the surgeon pulls on tubular member 44 which tears weakened region 42, releasing the balloon 20 from the tunneling shaft 18 as he removes it from the incision by pulling on the tubular member 44. Other parts of the balloon dissection device, such as the tunneling shaft 18 and olive-shaped obturator 26, remain in the body of the patient.

The surgeon then releases the tunneling shaft 18 from the rest of the device by depressing levers 68 on the handle assembly 14. The surgeon advances the skin seal assembly 28 to the skin at the incision 128, rotates it and tightens the movable collar 30 which acts as a lock ring. The resulting air-tight seal permits optional, subsequent gas insufflation of the dissected space in the tissue. With the device screwed in place, the tunneling shaft 18 is withdrawn and removed from the patient's body by pulling the first end half 60 and second end half 62 of the handle assembly 14 away from the incision in the patient. Note that in this particular embodiment, withdrawing the tunneling shaft 18 also causes withdrawal of the cannula 16, first center half 64 and second center half 66 of the handle assembly 14 because the olive shaped obturator 26 which is fixed to the end of the tunneling shaft 18 is too large to slide through the opening in the obturator 24 of the cannula 16. Thus, only the trocar assembly section 110 remains in the patient's body, as shown in FIG. 8, thereby creating a port into the patient's body through which visualization and/or working instruments may be inserted.

Figure 8:
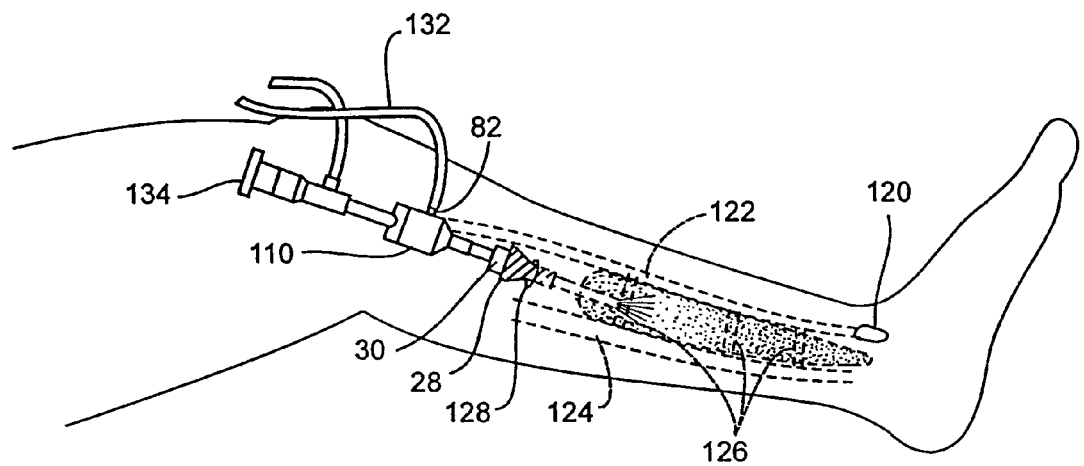
FIG. 8 is a schematic diagram which illustrates the insertion of an endoscope into the dissected space in the tissue after the balloon of FIG. 7 has been deflated and removed from the patient's leg.

Optionally but preferably, the space in tissue created by the dissecting balloon 20 may be insufflated as described below and as illustrated in FIG. 8. A $CO_2$ line 132 is connected to the stopcock 82 of the trocar assembly 80. The subfascial space is insufflated under medium to high flow to about 15 millimeters of mercury of pressure. If desired, the surgeon may insert an endoscope 134 through a center opening in the trocar assembly 80 of the trocar assembly section 110, as shown in FIG. 8.

Figure 9:
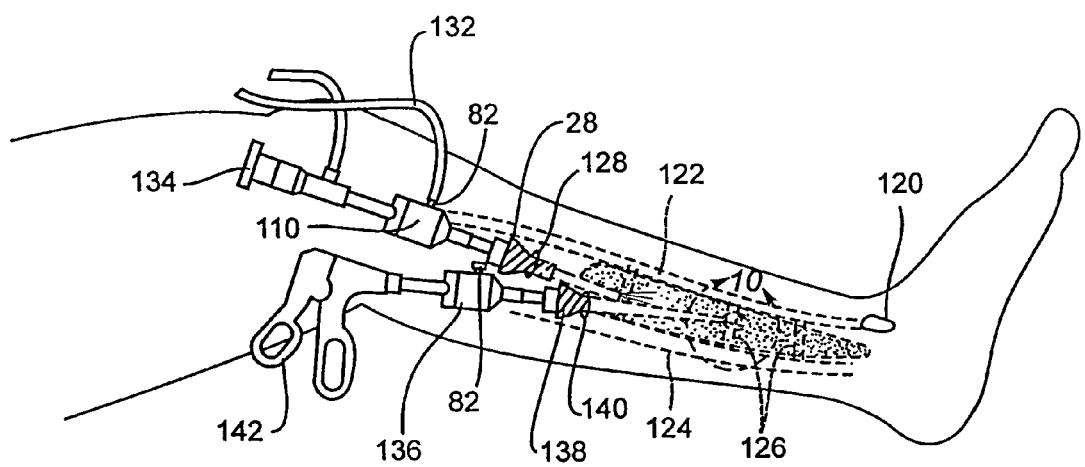
FIG. 9 is a schematic diagram which illustrates the partial performance of a SEPS procedure wherein a perforator vein is divided.
Figure 10:
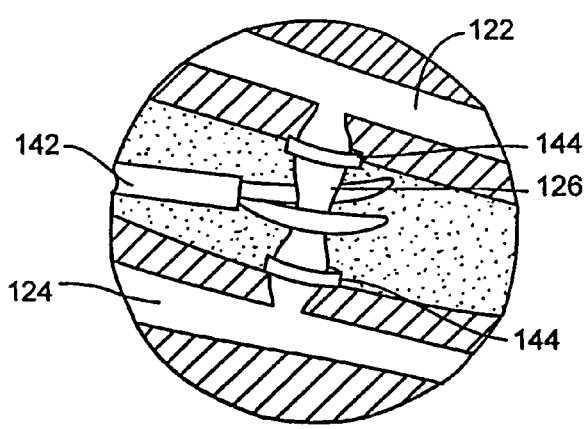
FIG. 10 is a schematic diagram showing a closeup view of the ligation and division of a perforator vein during a SEPS procedure.

Turning to FIG. 9, the surgeon may want a second port into the dissected space. The surgeon may make a second incision 140 in the leg and introduce a second trocar 136. The second trocar 136 has a skin seal assembly 138 which engages the skin at the second incision 140 to create an air-tight seal so that the insufflated space may be maintained. The surgeon can insert and use other instruments 142, such as a scissor, electrocauterizer, clipper, clamp or any other device, through the resulting port into the dissected space. As further examples, the surgeon may want to use an endoscope, an operating scope, a trocar, other diagnostic instruments, or other surgical instruments. By exposing the perforator veins, the surgeon can complete the SEPS procedure by ligating and/or dividing the perforator veins. FIG.

10 is a schematic diagram which shows a closeup view of an incompetent perforator vein 126 between the superficial vein 122 and the deep vein 124. The surgeon may clip the ends of the perforator vein 126 with clips 144. The incompetent perforator vein 126 may then be divided by surgical instrument 142. If the surgical instrument 142 is an electrocauterizer which is used to cauterize the perforator vein, any smoke which occurs in the dissected space may be evacuated by briefly opening the stopcock 82. After completing the SEPS procedure, the surgeon removes all instruments from the patient and closes the incisions 128, 140.

It is important to realize that not all of these steps must be performed, that additional steps may be added, and that some steps can be performed in a different sequence without departing from the scope of the present invention. For example, the step of gas insufflation of the dissected tissue is optional. As yet another example, the improved balloon device discussed herein may be used to cause further dissection of tissues which were previously dissected, e.g., by sharp dissection, blunt dissection and/or balloon dissection. As a further example, the improved balloon device may be used to cause no dissection at all, and instead, to merely retract already dissected tissue layers. From the foregoing, it can also be seen that the apparatus and methods of the present invention can be utilized in connection with various laparoscopic surgical procedures and in particular with subfascial endoscopic perforator surgical procedures. While embodiments and applications of the disclosed devices and associated methods have been shown and described, it will be apparent to those skilled in the art that the foregoing specific embodiments can be modified without departing from the scope of the present invention. Thus, the present invention shall be accorded the full scope of the claims appended hereto.

What is claimed is:

1. An apparatus for dissecting tissue to facilitate a laparoscopic surgical procedure in an anatomical region of a patient's body, the apparatus comprising:
   (a) a cannula having an end which is insertable through a laparoscopic incision in the patient's body;
   (b) a deflated inflatable balloon coupled to the cannula, the balloon having a distal end, a proximal end, and a neck portion adjacent the proximal end, where a width of the inflated balloon is at a maximum at the proximal end adjacent the neck portion and immediately decreases towards the distal end of the balloon and causes a non-uniform dissection of tissue, and a portion of the balloon is inverted into another portion of itself to reduce the length of the deflated balloon; and
   (c) a lumen which provides access to the interior of the balloon for inflating the balloon with a fluid.

2. The apparatus of claim 1 wherein the balloon upon inflation causes the non-uniform dissection of tissue in that a characteristic of the dissection is not identical throughout the dissection.

3. The apparatus of claim 1 wherein the characteristic of the dissection is the amount of the dissection.

4. The apparatus of claim 1 further comprising a seal mounted to the cannula, the seal providing an air-tight seal between the anatomical region of the patient's body in which the balloon is used and the exterior of the patient's body.

5. The apparatus of claim 1 wherein the balloon upon inflation has a non-tapered portion and a tapered portion.

6. The apparatus of claim 5 wherein the balloon has a distal portion and the tapered portion is located at the distal portion of the balloon.

7. The apparatus of claim 1 wherein the balloon has a tapered portion, the tapered portion having a distal portion which is small enough upon inflation to dissect tissue near the patient's ankle.

8. The apparatus of claim 1 wherein the balloon in its deflated state is gathered about the cannula.

9. The apparatus of claim 1 further comprising a handle coupled to the cannula, the handle comprising a first section and a second section, the first section of the handle permitting removal of a first part of the apparatus from inside the patient's body and the second section of the handle permitting removal of a second part of the apparatus from inside the patient's body.

10. The apparatus of claim 9 wherein the first section of the handle removes at least a portion of the cannula from the patient's body.

11. The apparatus of claim 1 further comprising a handle coupled to the cannula, the handle comprising a plurality of sections where each section of the plurality of sections permits the removal of a respective part of the apparatus from inside the patient's body such that a port providing access into the patient's body remains after use of the plurality of sections to remove the parts of the apparatus from the patient's body.

12. The apparatus of claim 1 further comprising a valve coupled to the cannula, the valve controlling the passage of a fluid for insufflating the dissected tissue.

13. An apparatus for dissecting tissue to facilitate a laparoscopic surgical procedure in a patient's body comprising:
   (a) A cannula having an end which is insertable through a laparoscopic incision in the patient's body;
   (b) A deflated inflatable balloon mounted to the cannula, the balloon having a distal end, a proximal end, and a neck portion adjacent the proximal end, where the width of the distal end of the balloon is smaller than the width of the proximal end of the balloon such that the inflated balloon is generally tapered from the proximal end towards the distal end, and a portion of the balloon is inverted into another portion of itself to reduce the length of the deflated balloon; and
   (c) a lumen which provides access to the interior of the balloon for inflating the balloon with a fluid.

14. The apparatus of claim 13 further comprising:
   a handle coupled to the cannula, the handle comprising a plurality of sections where each section of the plurality of sections permits the removal of a respective part of the apparatus from inside the patient's body such that a port providing access into the patient's body remains after use of the plurality of sections to remove the parts of the apparatus from the patient's body.

* * * * *